United States Patent
Johansson et al.

(10) Patent No.: US 7,988,715 B2
(45) Date of Patent: *Aug. 2, 2011

(54) SYSTEM AND METHOD FOR THERAPY AND DIAGNOSIS COMPRISING TRANSLATORY DISTRIBUTOR FOR DISTRIBUTION OF RADIATION

(75) Inventors: Thomas Johansson, Malmö (SE); Charlotta Eker, Lund (SE); Jörgen Malmborg, Lund (SE); Lasse Wesseltoft Mogensen, Soborg (DK); Sune Svanberg, Lund (SE); Marcelo Soto Thompson, Malmö (SE); Stefan Andersson Engels, Höör (SE)

(73) Assignee: SpectraCure AB, Lund (SE)

( * ) Notice: Subject to any disclaimer, the term of this patent is extended or adjusted under 35 U.S.C. 154(b) by 1247 days.

This patent is subject to a terminal disclaimer.

(21) Appl. No.: 10/556,806

(22) PCT Filed: May 14, 2004

(86) PCT No.: PCT/SE2004/000755
§ 371 (c)(1), (2), (4) Date: Oct. 2, 2006

(87) PCT Pub. No.: WO2004/101069
PCT Pub. Date: Nov. 25, 2004

(65) Prior Publication Data
US 2007/0060982 A1 Mar. 15, 2007

(30) Foreign Application Priority Data

May 14, 2003 (SE) ...................................... 0301406
May 14, 2003 (SE) ...................................... 0301410

(51) Int. Cl.
*A61N 5/06* (2006.01)

(52) U.S. Cl. ................ 607/88; 607/94; 607/100; 385/16

(58) Field of Classification Search .............. 607/88–94, 607/96, 100–102; 385/15–24; 350/96.2; 606/8–16; 128/898
See application file for complete search history.

(56) References Cited

U.S. PATENT DOCUMENTS

| | | | | | |
|---|---|---|---|---|---|
| 4,496,211 | A | * | 1/1985 | Daniel | 385/31 |
| 4,669,467 | A | * | 6/1987 | Willett et al. | 606/7 |
| 5,268,975 | A | * | 12/1993 | Yoshitani et al. | 385/22 |
| 7,151,869 | B2 | * | 12/2006 | Fernando et al. | 385/16 |
| 2001/0055462 | A1 | * | 12/2001 | Seibel | 385/147 |

FOREIGN PATENT DOCUMENTS

| | | |
|---|---|---|
| EP | 0280397 | 8/1988 |
| EP | 0523417 | 1/1993 |
| EP | 1314451 | 5/2003 |
| JP | 4343317 | 11/1992 |
| WO | WO 02074339 | 9/2002 |
| WO | WO 03041575 | 5/2003 |

* cited by examiner

OTHER PUBLICATIONS

Thomas Johansson, et al, Feasibility study of a system for combined light dosimetry and interstitial photodynamic treatment of massive tumors, Applied Optics, vol. 41, No. 7.

*Primary Examiner* — Ahmed M Farah
(74) *Attorney, Agent, or Firm* — Knobbe Martens Olson & Bear LLP

(57) ABSTRACT

A system and method for interactive interstitial photo-dynamic tumour therapy and/or photothermal tumour therapy of a human or animal, said system comprising at least one radiation distributor, which is arranged for distribution of optical radiation from at least one radiation source to a reaction site, or from the reaction site to at least one radiation sensor. The radiation distributor comprises at least one translatory displacement element being translatory movable relatively to another element. First ends of first radiation conductors are fixed to the first translatory displacement element and first ends of second radiation conductors are fixed to the other element, wherein the first and the second radiation conductors are connectable to each other in different constellations through translatory movement of the translatory displacement element and the other element relative each other in order to obtain different operation modes of said system.

24 Claims, 5 Drawing Sheets

SYSTEM AND METHOD FOR THERAPY AND DIAGNOSIS COMPRISING TRANSLATORY DISTRIBUTOR FOR DISTRIBUTION OF RADIATION

FIELD OF THE INVENTION

The invention relates generally to a system and a method for therapy and diagnosis in a subject. More particularly, the system and method relate to a system and method for tumour therapy and diagnosis in a human or animal. Even more particularly, the invention relates to a system and method for preferably interactive photodynamic therapy (PDT) and/or photothermal therapy (PTT) and/or photodynamic diagnosis (PDD) of a site on and/or in a human or animal, wherein electromagnetic non-ionising radiation is conducted to the site for reaction with the radiation, wherein the system comprises a distributor of radiation from at least one source of radiation to a reaction site, and from the reaction site to at least one radiation sensor, respectively, and wherein the reaction site preferably is a tumour site with a tumour, such as a malignant tumour.

BACKGROUND OF THE INVENTION

Within the field of medical therapy of tumour diseases, a plurality of treatment modalities has been developed for the treatment of malignant tumour diseases: operation, cytostatic treatment, treatment with ionising radiation (gamma or particle radiation), isotope therapy and brachytherapy employing radioactive needles are examples of common treatment modalities. In spite of great progress within therapy, the tumour diseases continue to account for much human suffering, and are responsible for a high percentage of deaths in western countries. A relatively new treatment modality, photodynamic therapy, commonly abbreviated PDT, provides an interesting complement or alternative in the treatment field. A tumour-seeking agent, normally referred to as a precursor or sensitizer, is administered to the body e.g. intravenously, orally or topically. It generally accumulates in malignant tumours to a higher extent than in the surrounding healthy tissue. The tumour area is then irradiated with non-thermal red light, normally from a laser, leading to excitation of the sensitizer to a more energetic state. Through energy transfer from the activated sensitizer to the oxygen molecules of the tissue, the oxygen is transferred from its normal triplet state to the excited singlet state. Singlet oxygen is known to be particularly toxic to tissue; cells are eradicated and the tissue goes in necrosis. Because of the localisation of the sensitizer to tumour cells a unique selectivity is obtained, where surrounding healthy tissue is spared. The clinical experiences, using in particular haematoporphyrin derivative (HPD) and delta aminolevulinic acid (ALA) have shown good results.

Sensitizers may also exhibit a further useful property; when the substance is excited with visible or ultraviolet radiation, it will yield a characteristic fluorescence signal, shifted towards longer wavelengths. This signal clearly appears in contrast to the endogenous fluorescence of the tissue, which is also called autofluorescence, and is used to localise tumours and for quantifying the size of the uptake of the sensitizer in the tissue.

The limited penetration in the tissue of the activating radiation is a big drawback of PDT. The result is that only tumours less than about 5 mm thickness can be treated by surface irradiation. In order to treat thicker and/or deep-lying tumours, interstitial PDT (IPDT) can be utilised. Here, light-conducting optical fibres are brought into the tumour using, e.g. a syringe needle, in the lumen of which a fibre has been placed.

In order to achieve an efficient treatment, several fibres have been used to ascertain that all tumour cells are subjected to a sufficient dose of light so that the toxic singlet state is obtained. It has been shown to be achievable to perform dose calculations of the absorptive and scattering properties of the tissue. E.g., in the Swedish patent SE 503 408 an IPDT system is described, where six fibres are used for treatment as well as for measurement of the light flux which reaches a given fibre in the penetration through the tissue from the other fibres. In this way an improved calculation of the correct light dose can be achieved for all parts of the tumour.

According to the disclosure of SE 503 408, the light from a single laser is divided into six different parts using a beamsplitter system comprising a large number of mechanical and optical components. The light is then focused into each of the six individual treatment fibres. One fibre is used as a transmitter while the other fibres are used as receivers of radiation penetrating the tissue. For light measurement light detectors are mechanically swung into the beam path which thus is blocked, and the weak light, which originates from the fibres that collected the light which is administered to the tissue, is measured.

However, such open beam paths result in a strongly lossy beamsplitting and the resulting losses of light drastically impair the light distribution as well as the light measurement. Furthermore, such a system must often be adjusted optically, which is also an important drawback in connection with clinical treatments. The system is also large and heavy and difficult to integrate into a user-friendly apparatus. Moreover, it is difficult to control the power of the light sent into each individual fibre, which makes the measurement results unreliable.

A solution to these problems has been proposed in PCT/SE02/02050, wherein a distributor for radiation having two discs rotating relative each other is described. The radiation distributor couples optical fibres between different operation modes. For switching between several light sources to one fibre going to the patient, an assembly with a total of four discs is described. There is a need to further reduce the size of the described solution in order to further minimise the size of the system.

EP-A1-0523417 discloses a pipeline switch for distribution of radioactive emitters and/or test objects for radiotherapy, i.e. radioactive radiation treatment of a body. The emitters or test objects are conveyed within pipelines on flexible wires movable within the conduit. First pipes for conveying the flexible wires to the switch are on the one hand connected to a moveable switch element and second pipes further conveying the flexible wires to the body connected to a second, stationary switch element. The two switch elements are moveable relative each other and different constellations of pipelines are thus possible. However, when changing from one constellation to another, the flexible wire has to be retracted between each switching process, otherwise the relative movement of the switch element is obstructed. Switching times and treatment times are thus very long. Furthermore, the pipelines are not suitable for conducting radiation themselves, they just provide external protection and guidance to the flexible wires conveyed therein. The construction is also bulky and not suited for small optical fibres. Moreover, the arrangement of the disclosure is not suited for diagnosis, only for therapy, and no interactive co-operation is disclosed.

EP-A2-0280397 discloses a sterilizable endoscope having a central coherent fibre bundle for carrying an image to a viewing means. The fibre bundle is further surrounded by a large number of light fibres. The proximate end of the endoscope is provided with a coupling means for aligning the optical fibre bundle with the optical system of the viewing means and for providing an interface with light transmitting means to transmit light from a light source along the light fibres to a body cavity to be inspected. The device can be used for detection of cancer cells and treatment thereof by phototherapy. A dye is administered to the tissue being examined and subsequently exposed to an exciting laser light frequency. Cancer cells will emit fluorescent light which is detected and displayed on the video monitor and the same light frequency as this fluorescent light is then transmitted through the light fibres to the cell for phototherapy treatment. However, only the use of a single wavelength light source is disclosed, it is thus not possible to have multiple diagnostics performed without manually exchanging the light source. Moreover, it is not possible to switch between different constellations of the light fibres, i.e. all fibres always have the same function (light in or light out). The coupling means mentioned in EP-A2-0280397 is only used to adjust the path of light through a two-part endoscope when it is assembled prior to use. In addition, different fibres are used for directing therapeutic light to a cancer location and to direct diagnostic light back through the endoscope no distribution is performed between different operating modes. This solution offers for instance no neither interactive treatment nor mapping of tumours. Thus, there is a need for a new compact device allowing distributing of radiation in a system for therapy and diagnosis in a human or animal, wherein the therapy and diagnosis comprises PDT, PTT, and PDD. Moreover, a further problem to be solved by the invention is to provide an alternative solution with regard to the prior art.

SUMMARY OF THE INVENTION

The present invention overcomes the above identified deficiencies in the art and solves at least the above identified problems by providing a system and a method according to the appended patent claims, wherein a very practical and efficient implementation of interactive IPDT is achieved in that different optical measurements for diagnostics and dosimetry can be performed in an integrated and simple way. An important application of the invention is interactive, interstitial photodynamic therapy, and/or interactive photothermal tumour therapy. According to the invention, the size of a system using existing optical radiation distributors, such as described in PCT/SE02/02050 is further reduced. Moreover, the invention allows such an existing optical radiation distributor to improve switching functionality with a reduced overall size of such a distributor. Losses for diagnostic light are reduced as at least one site of attenuation, i.e. one extra switch, is eliminated according to one embodiment of the invention. The invention offers also increased flexibility and reduces the influence of mechanical tolerances. Furthermore, the invention is an alternative solution to the problems and drawbacks associated with the systems according to the prior art.

The term "radiation" used hereinafter in this specification refers to radiation suitable for the field of the invention, i.e. for photodynamic therapy (PDT) and/or photothermal therapy (PTT) and/or photodynamic diagnosis (PDD). More specifically this radiation is "optical" radiation, i.e. non-ionising electromagnetical radiation within the wavelength-range of infrared (IR) visible or ultraviolet light. This also concerns radiation sources, radiation conductors, radiation sensors, radiation switches etc. within the scope of the embodiments and claims defining the invention, i.e. these sources, conductors or sensors for "radiation" are adapted to generate, conduct, measure, etc. the above-mentioned non-ionising radiation.

According to one aspect of the invention, a system for therapy and/or diagnosis of a human or animal comprises at least one radiation distributor, which comprises at least one longitudinal translatory displacement element, such as a sliding sledge, having preferably at least two parts translatory displaceable relative each other for coupling a plurality of radiation conductors in different constellations for different operating modes of the system. Switching between the different constellations for different operating modes of the system is carried out by displacing at least one longitudinal translatory element, i.e. by motion of the longitudinal translatory element along its longitudinal axis relative the other part. Thus operations such as coupling of one radiation source to a single output radiation conductor and/or coupling of a plurality of radiation conductors from a site in a human or animal to at least one radiation detector are accomplished in an effective way by means of a system comprising a compact translatory switching device.

One longitudinal translatory displacement device element may be fixed and the other movable or both are movable relative each other, e.g. with relation to a fixed housing.

BRIEF DESCRIPTION OF THE DRAWINGS

In order to explain the invention more detailed, a number of embodiments of the invention will be described below with reference to the appended drawings, wherein.

DESCRIPTION OF EMBODIMENTS

Figure 1:
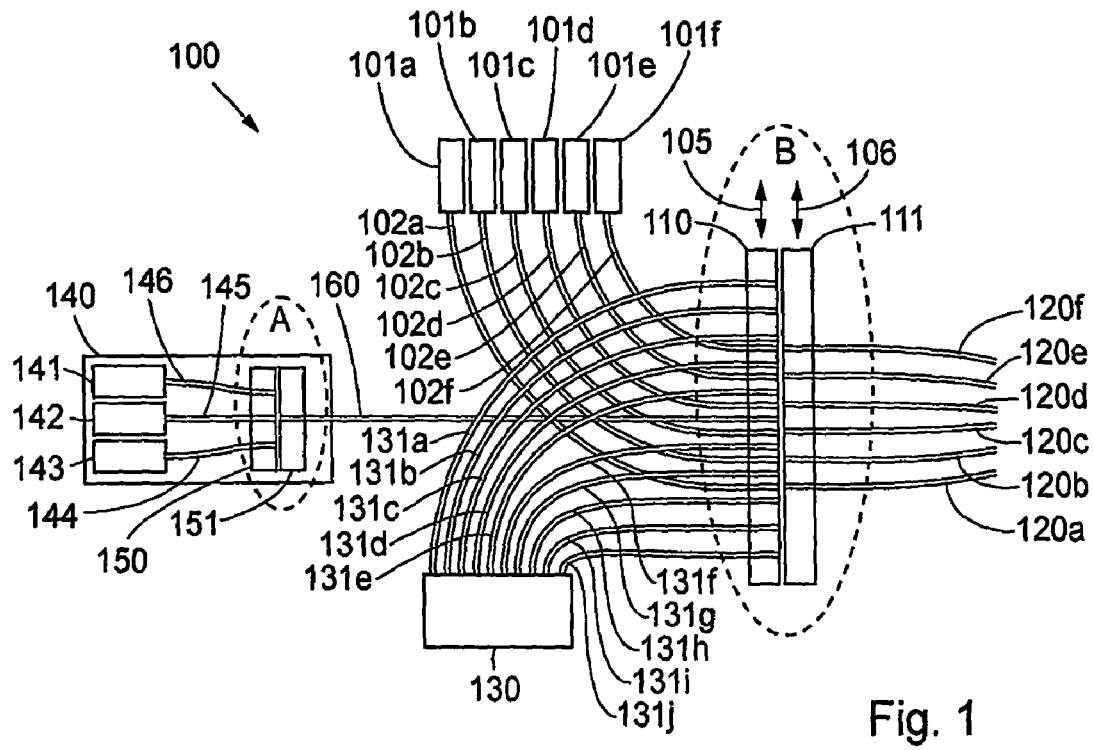
FIG. 1 is a schematic view illustrating an embodiment of the invention in the tumour therapeutic mode, in a system according to the invention, wherein light guides are arranged interstitially inserted in a tumour.

FIG. 1 is a schematic view illustrating an embodiment of the invention in a system according to the invention. In order to simplify the description of the embodiments, reference numerals for similar elements shown in the figures are not repeated in all figures. An embodiment 100 of the distributor of the system according to the invention is now described with reference to FIGS. 1-4 and FIG. 9. A distributor 1 for radiation comprises two substantially in close proximity to each other lying longitudinal longitudinal translatory elements made of, e.g. 1 cm thick steel or a some mm thick composite material, depending on different parameters, such as the way of fastening the radiation conductors to the translatory elements. When a contact element, such as conventional optical fibre couplings are used for fixing the radiation conductors to the longitudinal translatory elements, these couplings ensure the mechanical stability and define the size of the elements. In case the radiation conductors are optical fibres directly attached to the longitudinal translatory elements, the elements are more compact. In the case of a micromechanical realisation of the longitudinal translatory elements, even smaller dimensions are obtained. The longitudinal translatory elements are hereby arranged in such a manner that they may move longitudinally translatory relative to each other in such a manner that a plurality of radiation conductors 144-146 or 102a-102f, 131a-131j, 160 respectively, such as optical fibres, being fixed to holes 2 in the first longitudinal translatory element 110, 150 are coupled to a second plurality of fibres 160 or 120a-120f respectively, being fixed to holes 2 in the second longitudinal translatory element 111, 151, by appropriately positioning the two elements relative to each other. The system 100 shown in FIG. 1 comprises two such radiation distributors A and B comprising the longitudinal translatory elements 110, 111, 150, 151. These elements are shown as longitudinal elements in FIGS. 1 to 4. However, they may have another geometrical shape, as can be seen in FIGS. 5-8. Furthermore, at least one of the elements may be integrated into a housing etc. The elements may be sledges, for coupling either treatment radiation or diagnostic radiation conducted through the radiation conductors to a patient.

In the diagnostic position radiation is coupled to at least one radiation detector 130. The diagnostic part of system 100 comprises a 2-1, 3-1, ..., n-1 radiation distributor A, wherein n is the number of diagnostic light sources 141, 142, 143. The radiation distributor consists of two translatory displaceable elements 150, 151. Each of the two elements is displaceable with relation to the other translatory element, in such a manner that one diagnostic radiation source at a time is coupled to radiation conductor 160 and further to the site in the patient to be treated via a second radiation distributor B. This diagnostic mode will be described in more detail below, with reference to FIGS. 2 and 3. Furthermore a plurality of diagnostic radiation sources may be used simultaneously. In this case several diagnostic radiation sources may be modulated, so that the diagnostic radiation may be detected simultaneously by means of e.g. a lock-in method or by multiplexing the signals, wherein the therapeutic radiation preferably is shut off in diagnostic mode.

A main radiation distributor B comprises two translatory elements 110, 111. The two translatory elements 110, 111 are displaceable with relation to the other translatory element, as indicated by the arrows 105, 106. The displacement is controlled in such a manner that a plurality of radiation conductors 120a-120f lead radiation to and from a tumour site in a patient. Main radiation distributor B switches between the diagnostic operation modes and the therapeutic operation mode. The radiation conductors 120a-120f leading to and from the patient are fixed to the translatory element 111. The translatory element 110 of the main radiation distributor B comprises a (3N-1) to N radiation distributor, wherein N is the number of radiation conductors 120a-120f to/from the patient fixed in translatory element 111 and (3N-1) is the number of radiation conductors fixed in translatory element 110 of which N are radiation distributors 102a-102f coupled to light sources 101a-101f and 2(N-1) are radiation distributors 131a-131j coupled to radiation detector 130, and one, 160, is coupled to the diagnostic radiation source 240.

In the therapeutic mode, B is adjusted in such a manner, as shown in FIG. 1. Treatment radiation originating from the radiation sources 101a-101f is coupled to radiation conductors 102a-102f. These radiation conductors, such as light guides or optical fibres, are coupled to translatory displacement element 110. Element 110 is aligned with translatory displacement element 111 in such a manner that the light from light sources 101a-101f is coupled to radiation conductors 120a-120f and further to the treatment site in the patient.

Figure 2:
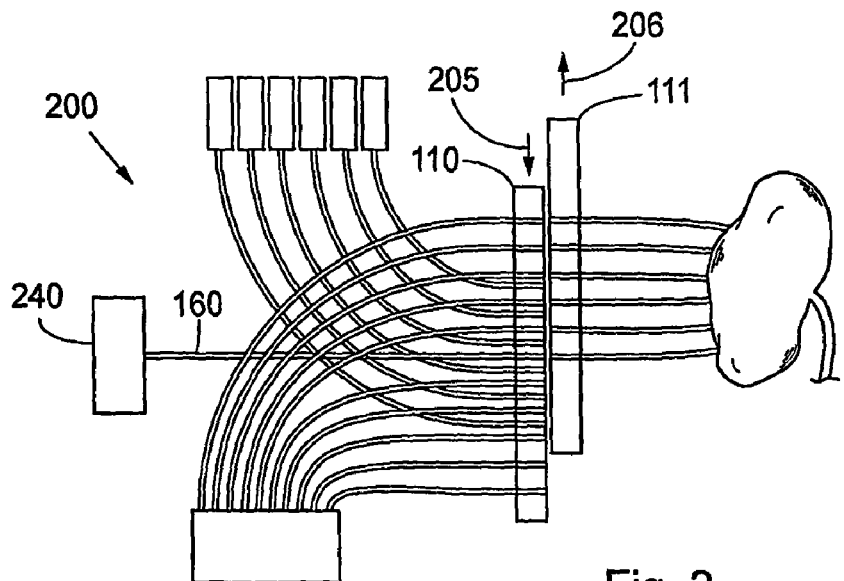
FIG. 2 is a schematic view illustrating another embodiment of the invention in the tumour diagnostic mode.
Figure 3:
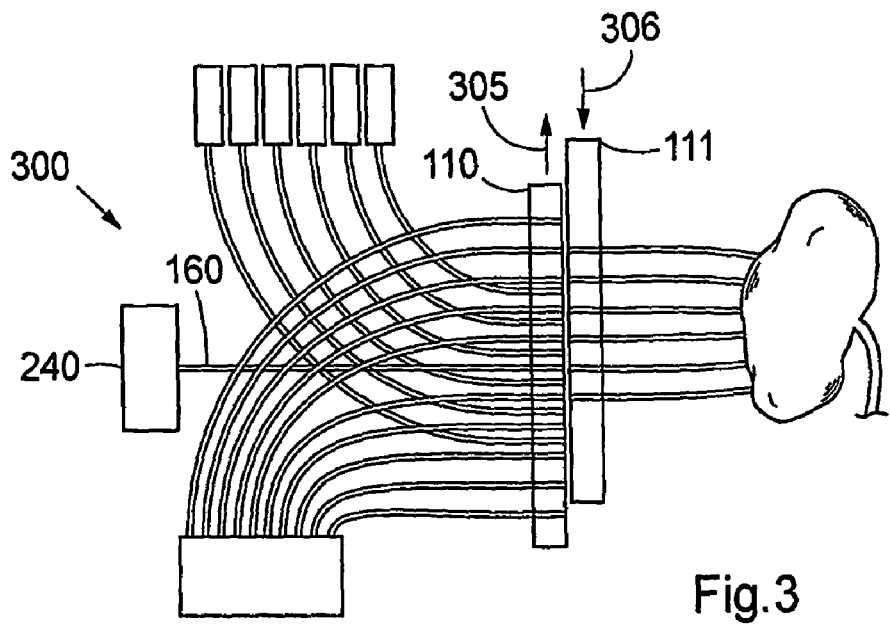
FIG. 3 is a schematic view of the embodiment according to FIG. 2 in another diagnostic mode.

In diagnostic mode the radiation distributor A is adjusted such that one of diagnostic radiation sources 141, 142, 143 is coupled to radiation conductor 160. Alternatively, only one diagnostic radiation source is used in the system, as shown in FIGS. 2 and 3. Main radiation distributor B is in diagnostic mode adjusted such that one of the N patient fibres 120a-120f is coupled to a diagnostic radiation source by means of radiation conductor 160. This is accomplished by transversally sliding the translator elements 110, 111 relative each other, as indicated by arrows 205, 206. The radiation, which is being transmitted back from the site in the patient through the remaining (N-1) radiation conductors from the plurality of radiation conductors 120a-120f, is also called diagnostic radiation. This diagnostic radiation is coupled to (N-1) radiation conductors from a plurality of radiation conductors 131a-131j leading to the radiation detector 130. Subsequently, the radiation distributor B is adjusted in such a way that another of the N patient radiation conductor 120a-120f is coupled to diagnostic radiation emitting fibre 160. This is accomplished by once again sliding the translator elements 110, 111 transversally relative each other, as indicated by arrows 305, 306. In this way another set of (N-1) radiation conductors is coupled to (N-1) radiation conductors from a plurality of radiation conductors 131a-131j leading to the radiation detector 130. This is repeated N times, until all N coupling combinations of radiation conductor 160 to the N patient radiation conductors, is accomplished. In case a plurality of n diagnostic radiation sources is present in the system, the N measurements are carried out with each of the n radiation sources, which results in (N*n) diagnostic measurements, each measurement delivering (N-1) measurement values. Alternatively to the sequence described above, the n radiation sources are applied subsequently, before switching to the next input radiation conductor to the patient. The detector may be a single detector or a plurality of detectors or an array detector.

Figure 4:
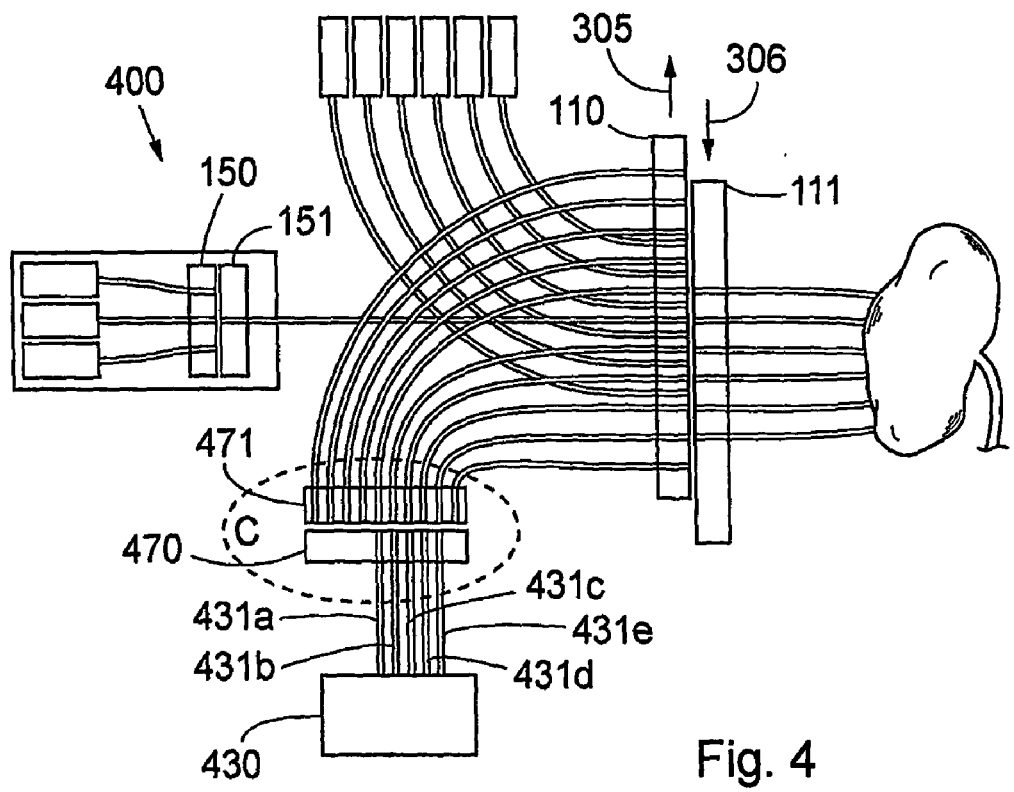
FIG. 4 is a schematic view illustrating a further embodiment of the system according to the invention with a radiation distributor coupling a radiation detector in diagnostic mode.

FIG. 4 is a schematic view over another embodiment according to a system of the invention, wherein a further radiation distributor C is used for minimising the number of radiation conductors leading to detector 430. Distributor C comprises two translatory elements 470, 471. The two translatory elements 470, 471 are displaceable with relation to the other translatory element respectively. A plurality of (N-1) radiation conductors 431a-431e, corresponding to the (N-1) radiation conductors conducting diagnostic radiation from the patient, are fixed to the translatory element 470 and lead to the detector 430. 2*(N-1) radiation conductors 131a-131j (as shown in FIG. 1 being connected to element 110 and detector 130, respectively) lead in this case from the translatory element 110 to the translatory element 471. Radiation distributor C is adjusted in such a manner that only the active (N-1) radiation conductors of the plurality of conductors 131a-131j are couple to the detector 430 through radiation conductors 431a-431e. Alternatively, the translatory element 471 may be integrated with the translatory element 110 and the translatory element 470 may be integrated with the translatory element 111 (not shown in the Figs.). In this way, the one and same translator may be used for therapy and diagnostic measurements.

N=6 and n=3 in the exemplary embodiments given above. However, other numbers of N and n are equally possible.

For calibration purposes of at least the mechanical part of the system according to the present invention, a $7^{th}$ hole may be present in translator 111. Preferably this hole is located exactly between radiation conductor 120d and 120c on translator 111, with reference to the linear translator shown in FIGS. 1-4. Concerning the disc 510 shown in FIGS. 5-8, the $7^{th}$ hole is preferably located anywhere in between holes 513 on the disc 510. The seventh hole is used to exactly define the position of an input radiation conductor in a hole on the opposite element of an radiation distributor. The seventh hole is either directly equipped with an radiation sensor or connected to a radiation sensor for detecting radiation transmitted from an radiation conductor facing the seventh hole from the opposite side. In this way the positioning of the elements of a radiation distributor may be calibrated. For instance the position of the seventh hole may be used to zero the position of stepping motors driving these elements. The seventh hole may equally be used to calibrate the position of translatory element 550 or any other translatory element of the system according to the invention in the same way.

For calibration purposes of the entire system according to the invention, including the radiation part, the overall performance of the system is recorded prior to the treatment by direct measurements on a calibrated tissue phantom made of, e.g., a sterile intralipid-water solution or a sterile solid phantom made of, e.g., Delrin®. The performance of the therapeutic radiation sources may either be monitored by internal and/or external power meters.

Figure 6:
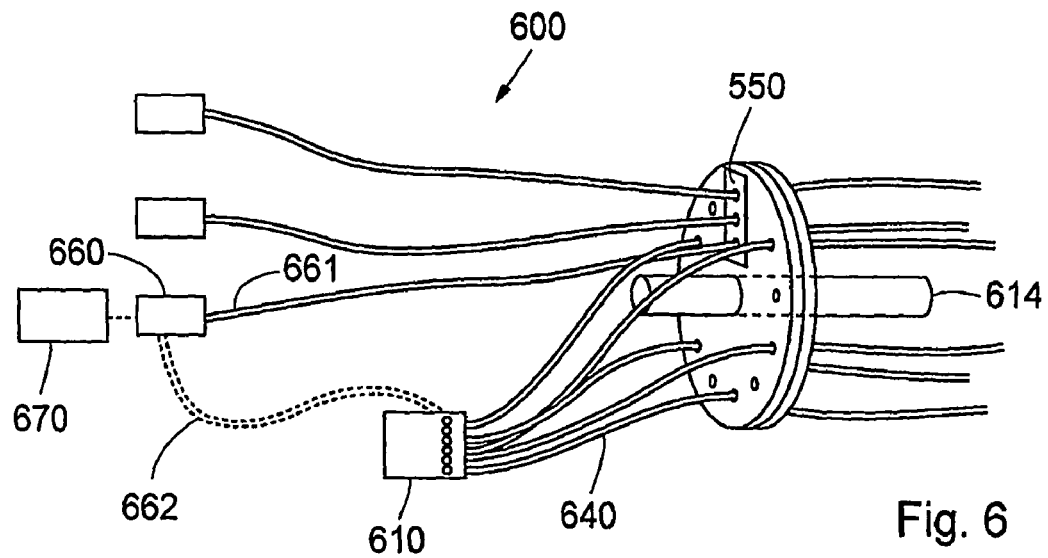
FIG. 6 is a schematic view showing the embodiment of FIG. 5 in a diagnostic mode.
Figure 7:
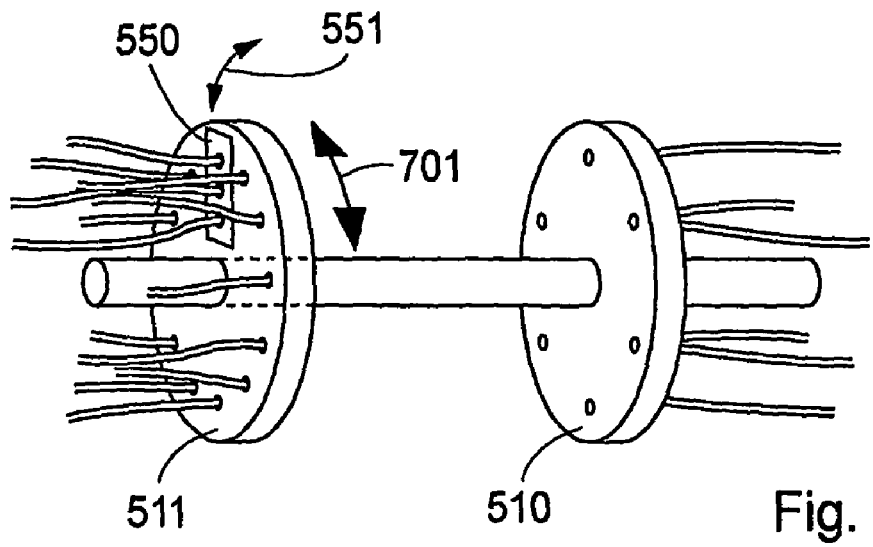
FIG. 7 is a schematic view showing the embodiment of FIG. 5 with discs of the rotatable radiation distributor taken apart.
Figure 8:
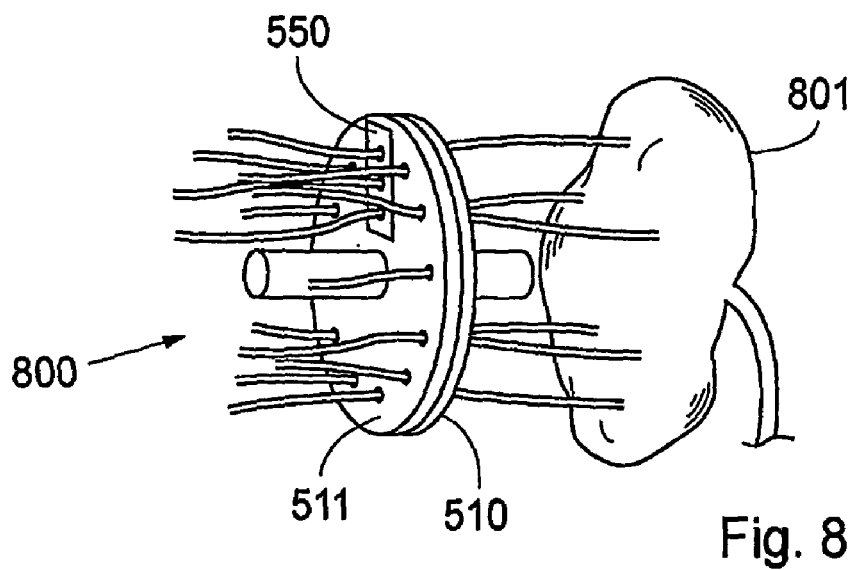
FIG. 8 is a schematic view illustrating the radiation distributors of FIG. 5 in use.
Figure 9:
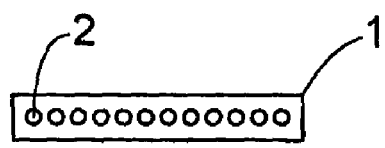
FIG. 9 is a planar top view over a longitudinal translatory radiation distribution element with holes for receiving light guides arranged in said element.

Another embodiment of the distributor of the system according to the invention is now described with reference to FIGS. 5-8. In this case, the longitudinally translatory element is integrated with another disc-based rotatable distributor, resulting in a more compact device compared to the prior art. In more detail, a disc-shaped distributor 500 comprises two flat and in proximity lying discs made of, e.g. 1 cm thick material such as steel, aluminium/titanium/magnesium, a composite material etc. The lighter the material is, the faster rotation of the discs between fixed positions is possible, while it is important that the discs at the same time are rigid and preferably durable. Discs of e.g. composite material are generally thinner than steel discs, e.g. some mm. The discs are hereby arranged on an axis 614, wherein one of the discs is a fixed disc 511 and the other one is a turnable disc 510, wherein the terms "fixed" and "turnable" are merely for the purpose of simplifying the present description. However, in order to simplify understanding of the function of distributor 500, disc 511 is exemplary defined as "fixed" and disc 510 is exemplary defined as "turnable" in the remainder of this description. In general, the two discs 510, 511 are rotatable relative each other. In use the discs 510 and 511 are arranged in close proximity against each other, as shown in FIG. 6 and FIG. 8 and for illustrative purposes separated from each other, as shown in FIG. 5 and FIG. 7.

Figure 5:
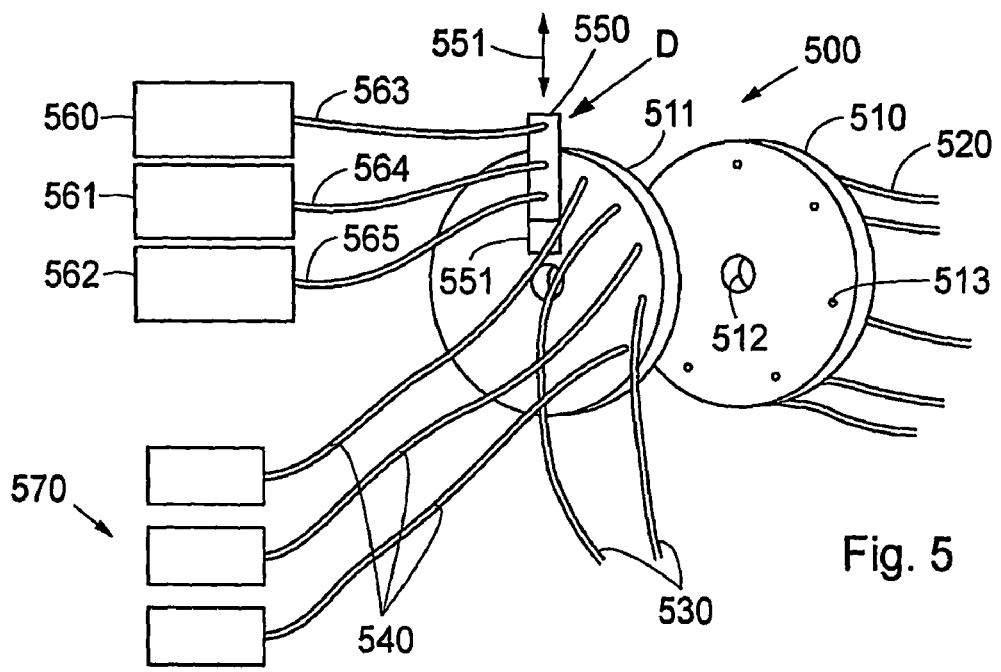
FIG. 5 is a schematic view illustrating yet another embodiment of the invention in use of the system according to the invention, with a longitudinal translatory radiation distributor integrated in a rotatable radiation distributor.

Evenly distributed holes 513 lying on a circle are arranged in both discs (FIG. 7) for fixation of radiation conductors 520 (referenced to an exemplary single radiation conductor of the plurality of fibres on the right of disc 510 in FIG. 5), 530, 540. Preferably the diameter of the holes is 0.1-0.7 mm in case the radiation conductors are optical fibres directly attached to the disc. In order to attain a high precision, allowing the light conductors to be arranged exactly face to face, the holes of the two discs can be drilled together, e.g. with a centering tube. Alternatively, high precision cutter or drilling machines may be used for producing the discs or any other mechanical elements mentioned in this description. Then the common axis 614 is utilised arranged at centrally located holes, exemplary referenced to as 512, of the discs 510, 511. It is thus possible to achieve a very high precision when making the series of holes.

By employing discs drilled together, radiation conductors can be fixed in said discs, wherein an extra, thinner disc then can be turned slightly, preferably spring-loaded, so that all radiation conductors are simultaneously pinched in their positions without the need for any glue or other fixation means. Alternatively, the diameter of the holes is made larger than the diameter of the radiation conductors, wherein the holes can be dressed with an appropriate piece of tubing, or the ends of the radiation conductors can be supplied with a fitted hose. Alternatively, the ends of the radiation conductors can be flared or flanged into the holes or the holes may be equipped with appropriate SMA connector or other type of connectors for receiving radiation conductors. The same principle applies to the holes 2 and fixation of radiation conductors in the translatory radiation distributors as described with reference to the previous embodiments or the current embodiment.

Preferably the radiation conductors are optical fibres, wherein different types of hoses or flexible tubes containing a radiation-conducting material are included. The radiation conductors should have such a length and be arranged in such a way that the discs can be turned a full turn (+−180 degrees) without problems. The direction of movement may be reversed to avoid the radiation conductors forming a spiral. The same principle applies to the translatory elements disclosed in this description, wherein the radiation conductors connected to the translatory elements should have such a length that the function of the translatory elements or the radiation conductors is not negatively influenced. Moreover, the length of the radiation conductors should be sufficiently long, that the positioning of the distal ends of the patient radiation conductors are not negatively influenced.

According to this embodiment of the invention, a plurality of first conductors 520 in a system for PDD, PDT and PTT are arranged in turnable disc 510 for conduction of radiation to and from a reaction site 801. By a reaction site we in the present context mean a site where photodynamically active compounds will react in a tumour when subject to therapy e.g., by being forwarded through the lumen of injection needles which are placed in the tumour, these radiation conductors 520 are then fixed in the reaction site 801. Then the radiation conductors are moved forward to arrive outside the distal end of the needle in the tumour tissue. The same light conductor 520 is used continuously during the treatment for integrated diagnostics and dosimetry (therapy) as well as to avoid that the patient be subjected to multiple pricks.

The holes 513 in the turnable disc 510 as well as in the fixed disc 511 are arranged on a circular line, wherein the circle radius on one disc equals the circle radius on the other disc. The holes on the turnable disc 510 are equally distributed along the circle line with an angular separation of $v_1=(360/n_1)$ degrees, where $n_1$ equals the number of holes, and the holes of the other, fixed disc 511 are equally distributed along the circle line with an angular separation $v_2$ equaling $(360/n_2)$ degrees. The first ends of the first radiation conductors 520 are fixed in the holes of the turnable disc 510, and first ends of the second radiation conductors 530, 540 are fixed in the holes of the fixed disc 511. In order to make the holes, and thereby the radiation conductors in both discs connectable to each other in different constellations by turning of the turnable disc 510, $n_2$ is selected to be a multiple of $n_1$, in such a way that $n_2$ is obtained as an integer larger or equal to 1. Suitably the number of holes in the fixed disc is chosen from two to more than six, e.g. two, three, four, five, six, seven, eight, nine or ten.

According to the currently described embodiment, six holes are arranged in the turnable disc 510 and twelve holes are arranged in the fixed disc 511, wherein, as mentioned above, the terms "fixed" and "turnable" are merely for explanatory reasons in order to simplify the description of the two discs being rotatable relative each other. With six first radiation conductors 520 the angular separation of the holes will accordingly become 60 degrees in the turnable disc 510 and with twelve holes arranged in the fixed disc 511 the angular separation will become 30 degrees for the second radiation conductors 540, 530.

According to the invention, a translatory sliding element 550 is arranged in the fixed disc 511 of the described system. The sliding element 550 is arranged in disc 511 such that it may be displaced radially outwards on disc 511 by a substantially radially translatory movement, as indicated by the arrow 551. Sliding element 550 receives radiation conductors, similarly as described above with reference to the attachment of fibres in the discs. Element 550 locks in place in such a position that transmission of radiation from one of radiation conductor 563, 564, 565 to a corresponding radiation conductor 520 is as little obstructed as possible, depending on the currently active radiation source 560, 561 or 562. In that way it is made possible to couple one radiation conductor at a time (564 in FIG. 5) from a plurality of radiation conductors 563, 564, 565 to a corresponding radiation conductor (reference numeral 520 in FIG. 5) in the turnable disc 510.

In order to facilitate the comprehension of the invention the following description of a preferred embodiment of the distributor of the system according to the invention relates to six first radiation conductors 520 arranged in the turnable disc 510 for conduction of radiation to and from the reaction site 801.

Thus, the fixed disc 511, as well as the turnable disc 510, have six holes 513 for corresponding second radiation conductors, and, for fixed disc 511, in addition, six further holes for second radiation conductors. All these radiation conductors can release radiation to the reaction site 801 and receive radiation from said site. Thus, several measurements can be recorded and read out simultaneously.

By turning the turnable disc 510 the first and the second radiation conductors become connectable to each other in different constellations. An exact positioning of the opposing radiation conductors in the distributor 500 is facilitated by arranging means for stopping the turnable disc 510 in predetermined angular positions, for instance, grooves may be arranged in the axis 614 for catching a spring-loaded ball arranged in the turnable disc 510 (not shown in the Figs.) or an angular detector on the rotatable disc can be used. Alternatively electronic regulation using stepper motors or servo motors may be used for this purpose, also in combination with the above described "seventh hole" method.

In order to allow a fast and efficient switching between a diagnostic mode and a therapeutic mode, every second of the second radiation conductors of the distributor 500 according to the invention, are divided into a first and into a second series. Both series of holes are arranged on the same circle, but displaced by 30 degrees with regard to each other. A specific radiation conductor in the first series of every other second radiation conductor is arranged for emitting radiation from at least one radiation source. The other, non specific radiation conductors in the first series of second radiation conductors are arranged for conduction of radiation to at least one radiation sensor 610. The second series of every other second radiation conductor is for therapeutical purposes arranged to emit radiation to the reaction site 801 from at least one radiation source.

The radiation conductors are preferably optical fibres, which in the distributor 500 shown in FIGS. 5-8 are connected to the fixed disc 511 as well as the turnable disc 510. Out of the radiation conductors, which are connected to the fixed disc 511, six radiation conductors can be used for diagnostic purposes and six can be used of therapeutical purposes. However, in the diagnostic mode, radiation from one to more than three modalities 560, 561, 562 can be employed.

With reference to FIGS. 5-6 only the presently described radiation conductors which are coupled to a turnable disc are for clarifying purposes shown; the other radiation conductors are not shown although they are coupled to said disc, as shown in FIGS. 7 and 8.

By turning the turnable disc 510 by 30 degrees the radiation conductor 520 which are optically coupled to the tissue of the patient can be employed for therapy as well as diagnostics and measurements. One out of every second radiation conductor fixed on disc 511 is in the diagnostic mode connected to different radiation sources for diagnostics, while the other five radiation conductors receive signals, which are related to the interaction of these radiation sources with the tissue. Radiation conductors 540 (not all six shown in FIG. 5) are connected to therapeutic radiation sources, e.g. lasers, whereas radiation conductors 530 are connected to radiation detectors. Radiation conductors 563-565 are coupled to diagnostic radiation sources 560-562.

Since intensity as well as spectral resolution is of interest, the distal ends of these five radiation conductors 640 are arranged in a slit-like arrangement so that they overlap the entrance slit and/or constitute the entrance slit of the radiation sensor 610, which may be a compact spectrometer or other type of detector and is supplied with a two-dimensional detector array or one to several one dimensional detector arrays. The recording range of the spectrometer is preferably within the range 400 to 900 nm. Each of the radiation conductors 530 can of course be connected to an individual radiation detector 610 in the form of a spectrometer or another type of detector, e.g. a compact integrated spectrometer.

With reference to FIG. 6, the assembly 600 is shown with the two discs 510, 511 on a common axle 614 and the translatory element 550 for switching between different diagnostic radiation sources is integrated in disc 511. In this way a more compact and robust construction is obtained compared to other solutions having an external radiation distributor for switching between the diagnostic radiation sources.

Preferably one of the radiation sources 560, 561, 562 is a laser of the same wavelength as the ones utilised for the laser irradiation for photodynamic tumour therapy, but could be of lower output power. Suitable filters can be arranged on radiation distributor 550, to be moved into the light path of the radiation sensor 610 in order to secure that the correct dynamic range is utilised for all measurement tasks.

Certain of the radiation sources 560, 561, 562 are utilised in order to study how radiation (light) of the corresponding wavelength is penetrating through the tissue of the tumour. When radiation from a radiation source is transmitted through the particular radiation conductor via radiation distributor 550 and the discs 511, 510 into the tissue, one of the first radiation conductors 520, which is the one opposing the radiation conductor in the distributor 550, will function as a transmitter in the tumour, and the other five radiation conductors 520 in the tumour will act as receivers and collect the diffuse flux of light reaching them. The radiation collected is again conducted via the discs 510, 511 and via radiation conductors 640 (whereof two conductors are shown in FIG. 5 at 530) to the radiation sensor 610 and five different light intensities can be recorded on the detector/detectors/detector array.

When the turnable disc 510 is turned by 60 degrees, the next radiation conductor 520 to the patient will get the role as transmitter, and the five others become the receivers for a new light distribution. After four further turns of the turnable disc 510, each by 60 degrees to the following radiation conductor 520 in the patient, radiation flux data for all remaining combinations of transmitters/receivers have been recorded. Thus, in total 6×5=30 measurement values are obtained and can be used as input data for a tomographic modelling of the radiation dose build up in the different parts of the tumour during the course of the treatment. Furthermore, by switching through the three light sources 560-562, by means of longitudinally translatory moving radiation distributor 550 in a substantially radial direction in the fixed disc 511, these 30 measurement values are multiplied by the number of radiation sources 560, 561, 562, resulting in 90 tomographic measurement values.

In addition to a specific wavelength, radiation from a white light source and/or broadband light emitting diodes and/or line light sources can be coupled into the particular active light conductor in radiation distributor 550. On passage through the tissue to the receiving radiation conductor 520 in the patient, the well-defined spectral distribution of the radiation source will be modified by the tissue absorption. Then, oxygenated blood yields a different signature than non oxygenated blood, allowing a tomographic determination of the oxygen distribution utilising the thirty different spectral distributions which are read out, five spectra at a time in the six possible different constellations on rotation of the turnable disc 510 during a diagnostic investigation. Such a determination of the oxygenation in the tumour is important, since the PDT process generally requires access to oxygen in the tissue.

Finally, a light source for blue/violet or ultraviolet light, e.g. a laser, can be coupled to the particular active radiation conductor in radiation distributor 550. Then fluorescence is induced in the tissue, and a sensitizer administered to the tissue displays a characteristic red fluorescence distribution in the red/near-infrared spectral region. The strength of the corresponding signal allows a quantification of the sensitizer level in the tissue.

Since the short wavelength light has a very low penetration into the tissue, the induced fluorescence will only be measured locally at the tip of the radiation conductor. For this task there is in this case for the corresponding radiation source 670 at the distal end of the particular radiation conductor 661 arranged a beamsplitter 660, connected via the radiation conductor 662 and which is preferably a dichroic beamsplitter, transmitting the exciting light but reflecting the red-shifted fluorescence light. This reflected radiation is focused into the distal end of a conveying radiation conductor 662, the other end of which is connected to the radiation sensor 610, which records the fluorescence radiation distribution. A suitable self-contained fluorosensor is described in Rev. Sci. Instr. 71, 510004 (2000). Such a system with dichroic beamsplitters may also in a similar way be implemented by means of the translatory radiation distributor system as shown in FIGS. 1-4. For instance radiation conductor 662 may be inserted between radiation detector 130 and a dichroic beamsplitter 660 being inserted in e.g. radiation conductor 144.

By rotating the turnable disc 510, the fluorescence that is proportional to the concentration of the sensitiser, can be measured sequentially at the tips of the six radiation conductors. Since the sensitizer is bleached by the strong red treatment radiation, being particularly strong just around the tip of the radiation conductor 520 conducting radiation to the patient, it is essential to make this measurement before the start of the treatment.

If the tips of the radiation conductors 520, 120*a*-120*f* in addition are treated with a material, the fluorescence properties of which are temperature dependent, sharp fluorescence lines are obtained upon excitation, and the intensity of the lines and their relative strength depend on the temperature of the tip of the radiation conductor 520, 120*a*-120*f* being employed for treatment. Examples of such materials are salts of the transition metals or the rare earth metals. Thus also the temperature can be measured at the six positions of the six radiation conductors, one at a time. The measured temperatures can be utilised to find out if blood coagulation with an associated radiation attenuation has occurred at the tip of the radiation conductor 520, 120*a*-120*f* and for studies regarding the utilisation of possible synergy effects between PDT and thermal interaction. Since the lines obtained are sharp, they can be lifted off the more broad-banded fluorescence distribution from the tissue.

The concentration of the sensitizer can for certain substances be measured in an alternative way. Then the red radiation used for the radiation propagation studies is used to induce near-infrared fluorescence. This fluorescence penetrates through the tissue to the tips of the receiving radiation conductors 520, 120*a*-120*f*, and are displayed simultaneously as spectra obtained in the radiation sensor 610, 130. A tomographic calculation of the concentration distribution may be performed based on in total thirty measurement values.

After diagnostic measurements and calculations have been performed, the radiation conductors 520 optically coupled to the tissue of the patients can be utilised for therapy by rotation of the turnable disc 510 by 30 degrees. Therapeutic radiation sources are thus coupled to the patient fibres 520. The therapeutic radiation sources are preferably laser sources with a wavelength, which is adapted to the absorption band of the sensitizer. At the photodynamic tumour treatment a dye laser or a diode laser is preferably used, with a wavelength which is selected with regard to the sensitizer employed. For Photofrin® the wavelength is 630 nm, for δ-aminolevulinic acid (ALA) it is 635 nm and for phthalocyanines it is around 670 nm. Many further sensitizers exist. The individual lasers are regulated during the treatment to a desirable individual output power. If desired, they may have built-in or external monitoring detectors.

The therapeutical treatment can be interrupted and new diagnostic data can be processed in an interactive method until an optimal treatment has been reached. This method can include synergy between PDT and hyperthermia, where an increased temperature is reached at increased fluxes of laser radiation. The whole process is controlled using a computer, which does not only perform all the calculations but also is utilised for regulation.

Figure 10:
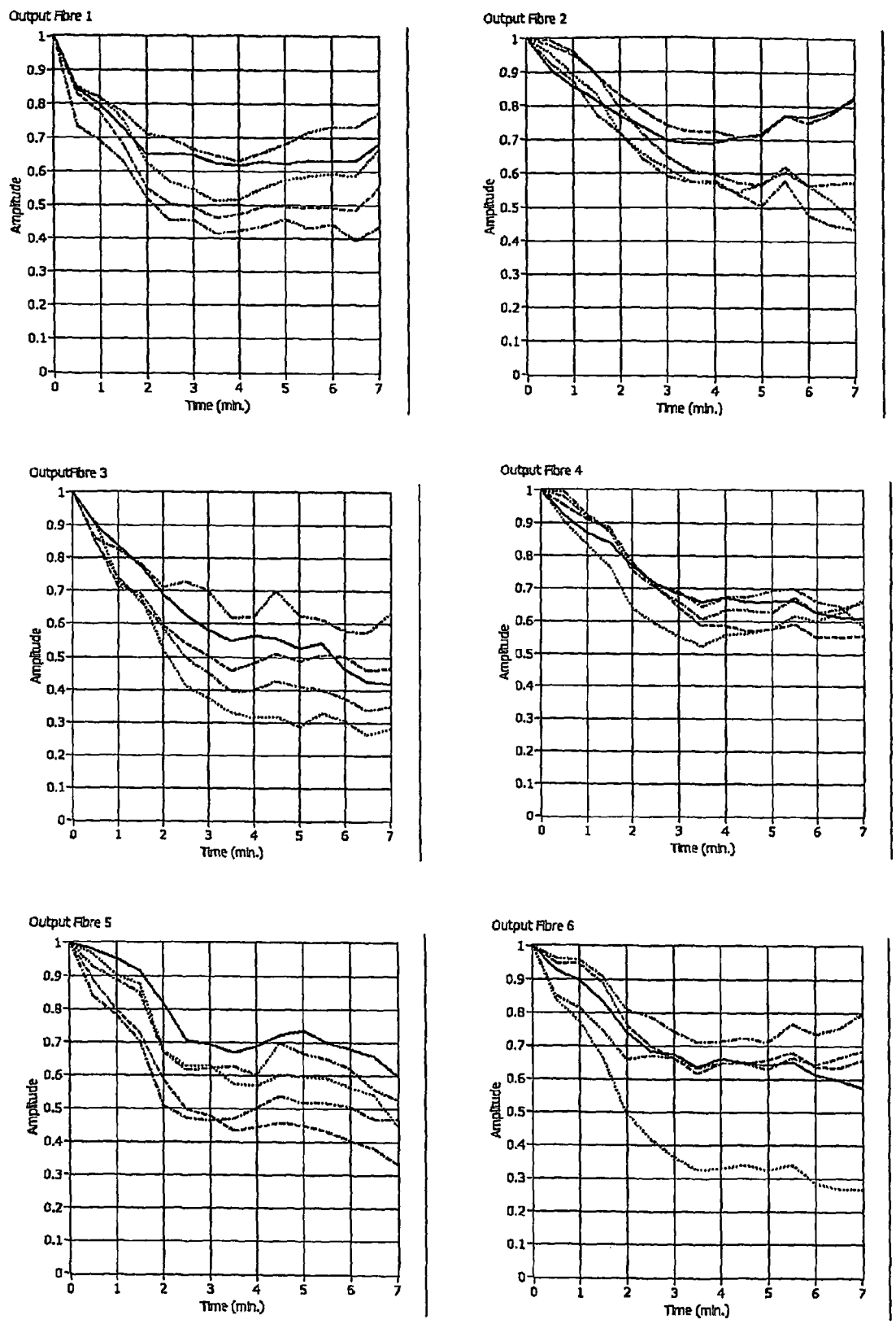
FIG. 10 are schematic graphs illustrating diagnostic measurements at different points of time during a tumour treatment performed with a practical realisation of an embodiment of the system in an exemplary practical application of the invention.

FIG. 10 are schematic graphs illustrating diagnostic measurements at different points of time during a tumour treatment performed with a practical realisation of an embodiment of the system in an exemplary practical application of the invention.

In every of these six diagrams one fiber end is used as an emitter and the other fiber ends act as collectors. From the emitting end radiation of wavelength 633 nm is emitted and the collecting ends transmit radiation to the detector(s) for quantification. All diagrams are normalized to the first sample. In the diagram "Output Fibre 1" is the radiation conductor 1 used as emitter and 2-6 are used as collectors. In the diagram "Output Fibre 2" is the radiation conductor 2 used as emitter and 1, and 3-6 are used as collectors, and so on. The measurements on the individual fibres are differetniated by different shapes of the curves. The output power from all emitting conductors is at all times equal. These diagram shows therefore how the transmittance of light of 633 nm wavelength changes versus time during the treatment. As can be seen, the transmittance is not constant during the progress of the diagnostic measurements. This information may also be used for enhanced diagnosis The radiation distributors described are preferably driven by stepper motors/servo motors in order to move between the different constellations.

Naturally, diagnosis and therapy may also be performed at the same time, if so desired. With an appropriate number of radiation conductors going to the tumour, for instance the above mentioned six radiation conductors for therapeutic irradiation plus four radiation conductors for simultaneously diagnosing the effect of the therapeutic light, it is possible to directly regulate therapy in real-time. This is of particular interest when performing therapy on sensitive organs that are not to be damaged by the therapeutic optical radiation. Of course it is a goal to only destroy tumour tissue. In the given example, the six radiation conductors illuminate the tumour tissue into which the distal ends of the six radiation conductors are placed. The four diagnostic radiation conductors are also placed into the tumour tissue at appropriate locations and pick up both the excitation radiation from the therapeutic radiation conductors scattered in the tumour tissue and the fluorescent radiation resulting in the tumour tissue. This picked-up radiation may be analysed in a spectrometer and be used for regulating the therapeutic radiation source. These, for example, four extra radiation conductors can be placed in-between the six radiation conductors for therapeutic irradiation. When the six radiation conductors are connected to the radiation sources the four extra radiation conductors are automatically connected to the radiation detector because of the arrangement of the translatory slides or rotating discs.

The present invention has been described above with reference to specific embodiments. However, other embodiments than the preferred above are equally possible within the scope of the appended claims, e.g. different shapes of the translatory elements than those described above, performing the above method by hardware or software, etc. Moreover, the translatory elements may be further minimised by using micromechanical technologies for constructing the elements. Thus, one realisation of the elements may be provided by a Micro-Electro-Mechanical System (MEMS) produced by microfabrication technology. The elements described may work according to different principles. One is the switching by direct fibre movement actuated by piezoelectric movement of the fibre in relation to output fibres. Another is the switching by microoptical beam deflection, which may be based on micromechanical components, such as microprisms or mirrors deflecting an optical beam to different output/input fibres. Piezosystem Jena Inc or Pyramid Optics Inc. provide suitable components based on the latter micromechanical principles.

Furthermore, the term "comprises/comprising" when used in this specification does not exclude other elements or steps, the terms "a" and "an" do not exclude a plurality and a single processor or other units may fulfil the functions of several of the units or circuits recited in the claims.

The invention claimed is:

1. A system for interactive interstitial photodynamic or photothermal tumor therapy or tumor diagnosis of a human, comprising; at least one first light source for emission of light within the wavelength-range of infrared (IR), visible or ultraviolet light; at least one light detector, for detection of light; and a plurality of optical fibers adapted to conduct light to or from a tumor site at or in said human, wherein the optical fibers, when in use, are employed as transmitters or receivers for conduction of light to or from the tumor site for therapy or diagnosis of a tumor at the tumor site; wherein at least one distributor adapted to distribute said light from at least the first light source to the tumor site, wherein the distributor comprises at least one longitudinal translatory element having a plurality of said optical fibers attached thereto and being arranged in such a manner that light is coupled in different constellations to or from said optical fibers for a diagnostic or therapeutic mode of said systems by longitudinal translatory movement of said longitudinal translatory element between pre-determined positions for aligning said optical fibers with a corresponding coupling element for transmitting or receiving said light to or from said light source or said light detector.

2. The system according to claim 1, wherein said system comprising at least one second light source for emission of therapeutic light through at least one of said optical fibers via said distributor via said longitudinal translatory element and said corresponding opposing coupling element to said tumor site.

3. The system according to claim 2, wherein the therapeutic light source is a light source for coherent light of a single fixed wavelength.

4. The system according to claim 2, wherein said operation modes of said system comprise a diagnostic operation mode, wherein one diagnostic light source is coupled via a first longitudinal translatory element to said first optical fibers transmitting diagnostic light to said site and the remaining first optical fibers are coupled to a light detector, and a therapeutic operation mode, wherein said therapeutic light sources are coupled to said first optical fibers transmitting therapeutic light to said site.

5. The system according to claim 4, wherein said at least one second longitudinal translatory element switches between the operating modes.

6. The system according to claim 1, further comprising a plurality of first optical fibers arranged for conducting light to or from the tumor site, a plurality of second optical fibers arranged for delivering light from at least one light source or transmission of light to said at least one light detector, and wherein said distributor is a distributor for distribution of light from at least one light source to the tumor site and/or from the tumor site to said least one light detector, wherein the opposing coupling element is a second longitudinal translatory element, and being arranged in such a manner that light is coupled in different constellations by translatory movement of a first if said translatory elements between pre-determined positions relative to the other said translatory elements.

7. The system according to claim 6, wherein each translatory element has holes arranged for receiving said optical fibers and that corresponding holes on the two translatory elements are equidistantly arranged on a straight line, and wherein said translatory elements are configured for transmitting light between the translatory elements.

8. The system according to claim 7, wherein first ends of the first optical fibers are fixed in the holes of a translatory displacement element and first end of second optical fibers are fixed in the holes in the second translatory element, wherein the first and second optical fibers are connectable to each other in different constellations through said longitudinal translatory movement between pre-determined positions of the longitudinal translatory displacement element and the second translatory element relative each other.

9. The system according to claim 1, further comprising first and second flat discs in close proximity, wherein said discs are turnable relative to each other, each disc having holes arranged in a circular line, wherein the circle radius on the first disc equals the circle radius on the second disc and wherein the holes in the first disc are equally distributed on a circle line with an angular separation of $V1=(360/n_1)$ degrees, n1 being the number of holes, and the holes in the other disc are equally distributed on the circle line with an angular separation of $n_2=(360/n_2)$ degrees, wherein $n_2=m \times n_1$, and wherein m is a multiple, which yields $n_2$ as an integer $>1$, and wherein first ends of optical fibers are fixed in the holes of the first disc and first ends of optical fibers are fixed in holes of the second disc except for one, whereby the optical fibers fixed to the first and second discs by rotation of the first turnable disc relative to the second disc are connectable to each other in different constellations, and wherein said longitudinal translatory element is arranged substantially radially outwardly movable and integrated with said first disc to couple between said plurality of optical fibers attached to said longitudinal translatory element to one of said optical fibers fixed to said second disc.

10. The system according to claim 9, wherein $n_1$ is the number of holes in the first disc of the distributor, $n_1=6$ and $m=2$, yielding $n_2=12$ holes in the second disc of the distributor.

11. The system according to claim 10, wherein every other fourth optical fiber is part of a first series of fourth optical fibers and that an optical fiber conductor in said first series of fourth optical fibers conductors being arranged for emitting light from the light source and the other optical fibers in said first series of fourth light conductors being arranged for transmission of light to the light detector.

12. The system according to claim 10, wherein first optical fibers being connected to diagnostic light sources, such that the longitudinal translatory element in said other disc couples one of said diagnostic light source to one of said third optical fibers in said first disc.

13. The system according to claim 9, wherein every second of said fourth optical fibers is part of a second series of fourth optical fibers arranged for emission of light from the light source.

14. The system according to claim 1, wherein the diagnostic light source comprises a beamsplitter.

15. The system according to claim 14, wherein light fiber is arranged between a dichroic beamsplitter and the light detector.

16. The system according to claim 15, wherein fluorescence is recorded through the same optical fiber as the one transmitting light to the tumor site.

17. The system according to claim 1, wherein at least one of the ends of the optical fibers is treated by a material with temperature sensitive fluorescence emission.

18. The system according to claim 17, wherein one or several of the optical fibers which are treated with the material with a temperature sensitive fluorescence emission are in use measuring the temperature at the tumor site, the light which is sent to the tumor site in use is heating the tumor site, and the intensity of the light is controllable by the measured temperature in order to regulate the temperature of the tumor site at the individual optical fibers.

19. A system according to claim 1, wherein the distributor comprises means for locking the light distributor into pre-determined transversal and/or azimutal positions.

20. The system according to claim 1, wherein said longitudinal translatory displacement element is an optical sledge.

21. The system according to claim 1, wherein at least one stepping motor or at least one servo system moves said elements of said light distributor relative to each other.

22. The system according to claim 1, wherein said operation modes are modes of the system comprised in the list of: interactive interstitial photodynamic tumor therapy, photothermal tumor therapy using hyperthermia, and tumor diagnostics, whereby these operation modes in use are alternated during the same occasion of treatment of said tumor site.

23. A method for interactive interstitial photodynamic tumor therapy of photothermal tumor therapy or diagnosis of a human, wherein at least one light detector and a plurality of optical fibers are connected to a tumor site and the optical fibers are used as a transmitter or a receiver for conduction of light to or from a tumor site for diagnosis and therapy of a tumor at the tumor site, wherein switching between tumor therapy and tumor diagnostics is achieved in an automated way by switching light fibers between constellations by means of a light distributor comprised in the system according to claim 1 and that the results from the diagnostics control the therapy process by regulating a therapeutic light intensity depending on the results of the diagnostics until an optimal treatment of the tumor site is achieved.

24. The method according to claim 23, wherein interactive interstitial photodynamic tumor therapy, photothermal tumor therapy using hyperthermia, and tumor diagnostics are alternatingly used during the same occasion of treatment of said tumor site.

\* \* \* \* \*

UNITED STATES PATENT AND TRADEMARK OFFICE
CERTIFICATE OF CORRECTION

PATENT NO. : 7,988,715 B2
APPLICATION NO. : 10/556806
DATED : August 2, 2011
INVENTOR(S) : Thomas Johansson et al.

Page 1 of 1

It is certified that error appears in the above-identified patent and that said Letters Patent is hereby corrected as shown below:

At page 1, after field (65) (Prior Publication Data) please insert:

--(60) Related U.S. Application Data

Provisional Application Nos. 60/470,856 and 60/470,854, both filed on May 16, 2003--.

At Column 5, Line 6, After "lying" delete "longitudinal".
At Column 13, Lines 8-9 (Approx.), Change "differetniated" to --differentiated--.
At Column 13, Line 16 (Approx.), After "diagnosis" insert --.--.
At Column 14, Line 53, In Claim 6, change "said least" to --said at least--.
At Column 15, Line 16 (Approx.), In Claim 9, change "n1" to --$n_1$--.
At Column 16, Line 18, In Claim 19, change "A system" to --The system--.
At Column 16, Line 20, In Claim 19, change "azimutal" to --azimuthal--.

Signed and Sealed this
Seventh Day of February, 2012

David J. Kappos
*Director of the United States Patent and Trademark Office*